United States Patent [19]
Pindera

[11] Patent Number: 4,679,933
[45] Date of Patent: Jul. 14, 1987

[54] DEVICE FOR BIREFRINGENCE MEASUREMENTS USING THREE SELECTED SHEETS OF SCATTERED LIGHT (ISODYNE SELECTOR, ISODYNE COLLECTOR, ISODYNE COLLIMATOR)

[76] Inventor: Jerzy T. Pindera, University of Waterloo, Department of Civil Engineering, Waterloo, Ontario, Canada, N2L 3G1

[21] Appl. No.: 397,921

[22] Filed: Feb. 28, 1983

[30] Foreign Application Priority Data

Jul. 14, 1982 [CA] Canada ................................. 407208

[51] Int. Cl.$^4$ ............................................. G01B 11/18
[52] U.S. Cl. ........................................ 356/35; 73/800
[58] Field of Search ................ 356/32, 33, 35; 73/800

[56] References Cited
PUBLICATIONS

Mazurkiewicz et al., "Integrated-Plane Photoelastic Method-Application of Photoelastic Isodynes", *Experimental Mechanics*, vol. 19, No. 7, pp. 225-234, Jul. 1979.

*Primary Examiner*—Davis L. Willis
*Assistant Examiner*—Matthew W. Koren

[57] ABSTRACT

A new method and device has been developed to determine experimentally the state and amount of birefringence along any arbitrary direction through a birefringent body. Such information can be used to determine the optical anisotropy of solid and liquid bodies, the residual and induced stress fields, etc. Essentially, this method and device separates, from the light scattered in all directions along an arbitrary path of laser light in a body, three sheets of light which are subsequently collimated; each of these light sheets contains parallel light rays carrying information of interest. The middle light sheet indicates the line of measurements, which is identical with the path or position of laser beam in a body. The two outer light sheets carry two complementary and independent pieces of information on the state and amount of birefringence along the line of measurements. Thus, both outer sheets of light can be used simultaneously to increase the reliability and accuracy of the birefringence measurements.

8 Claims, 6 Drawing Figures

DEVICE FOR BIREFRINGENCE MEASUREMENTS USING THREE SELECTED SHEETS OF SCATTERED LIGHT (ISODYNE SELECTOR, ISODYNE COLLECTOR, ISODYNE COLLIMATOR)

BACKGROUND OF THE INVENTION

1. Field of the Invention

This invention relates to the optical measurement methods in mechanics using scattered light techniques. Specifically, the invention relates to opto-mechanical apparatus which is useful for the rapid, accurate and theoretically correct measurements of the stress-induced birefringence, and, in particular, to determine cross-sections through elastic isodynes which carry information on the normal and shear stress components.

The measurements are simple when the patterns of light scattering are close to the Rayleigh model of scattering.

2. The Prior Art

There are several known methods of birefringence measurements using light scattered along the path of a narrow light beam (laser light), or a thin light sheet (laser light sheet). Depending on the technique of measurements one can distinguish the point-wise, line-wise, and whole field measurements (recordings). The point-wise measurements are usually expensive and require a costly measurement system. The line-wise measurements are usually performed in such a manner that the observation angle (see FIG. 2), vary from point to point along the path of the light beam; in addition, the location of the light beam in a body can not be recorded simultaneously on the same recording. The influence or existence of optical noise can not be detected and/or determined. The whole field measurements (recordings) are performed at the observation angles and azimuthal angles varying from point to point. Usually the image plane is not parallel to the selected object plane. As a result the intensity of scattered light is additionally modulated by the alterations of the observation angles and azimuthal angles; this unintentional modulation obscures the meaning of the recordings; in addition major portions of the intended object plane are out of focus. This leads to a recording of fringes, the intensity and geometry of which depends not only on the birefringence, but also on an undetermined transfer function of the measurement system and chosen experimental set-up. The collecting prism developed by J. T. Pindera improves incompletely the situation, since it inherently introduces an additional light modulation and a selective transmittance, which impair the signal/noise ratio.

OBJECT OF THE INVENTION

It is the aim of this invention to provide an essentially improved apparatus for measuring the state and amount of optical birefringence in an optically anisotropic body. This information is of primary use to determine the stress state in a solid body, the velocity vector field in a liquid, the residual stress states, and the residual orientational anisotropy.

Other objects of the invention will be apparent from the following description taken in connection with the attached drawings.

STATEMENT OF THE INVENTION

In accordance with the current invention, and as described in FIG. 1, I provide: (1) a source of radiant energy with frequencies in the range from visible to microwave, most preferably light from a laser, to produce a single narrow beam of collimated light; (2) means to circularly or linearly polarize the said light beam, and to adjust its plane of vibration, if applicable; (3) means to direct the said light beam, called primary light beam, into a birefringent body which internally scatters the said polarized light beam as it propagates along a chosen line of measurement inside the said body and modulates the intensity of the scattered light; (4) means to select from the said scattered light, and to collimate, three particular sheets of light, the intensity of which is optimally modulated by the parameters of birefringence of the said birefringent body along the line of measurements; (5) means to isolate a single sheet of scattered light; (6) means to select secondary sheets of light from the said primary sheets: the said secondary sheets, which only consist of parallel light beams carrying the pertinent information are subsequently focused; (7) means to reduce the optical noise carried by the said secondary light sheets and to produce images of intensity of light scattered from the primary light beam along the chosen line of measurement at the chosen azimuthal and observation angles; (8) means for displaying and/or recording of the said conditioned three light sheets.

THE DRAWINGS

DETAILED DESCRIPTION OF THE INVENTION

Theory of the Invention

Figure 1:
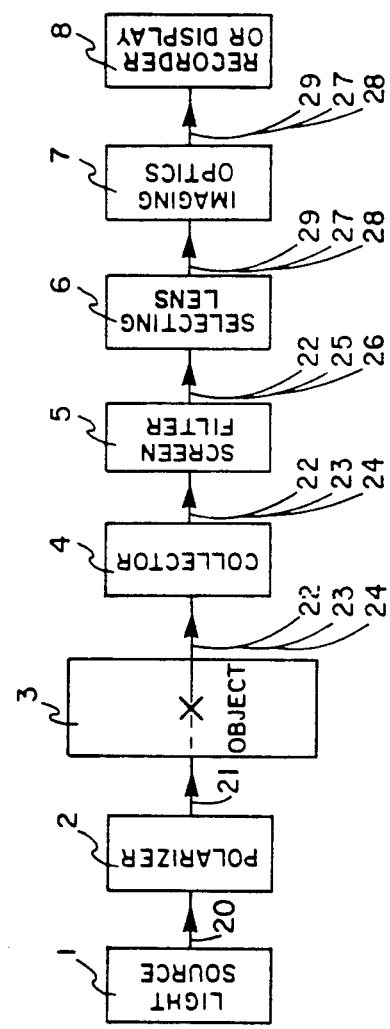
FIG. 1 is a block schematics of measurement system.

It is known in optics that the optical anisotropy (birefringence) of a body causes separation of the incident light beam into two wavefronts each of which propagating with a different velocity; the resulting distance between the two wavefronts can be described in terms of a linear relative retardation or an angular relative phase retardation. The magnitude of this retardation is directly related to the tensor of optical anisotropy. It is also known in optics that the relative retardation of the two wavefronts may be obtained from measurements of the intensity of light scattered in the selected directions in the optically anisotropic body.

The present invention relates to the apparatus performing measurements of the scattered light intensities in a manner which assures that the selected components of the optical anisotropy (birefringence) can be determined, simply and reliably, at any point along chosen lines within a birefringent body.

While the technique has application for a wide range of birefringence states, the following description is taken by way of example with respect to a particular birefringence state in a plate, whereas the optic axes are parallel to the face of a plate and the magnitude of birefringence in direction of plate thickness is constant. The term "radiant energy" as used herein denotes electromagnetic energy in frequency ranges from ultra-violet to microwaves. The information-collecting incident (primary) beam, parallel to the face of birefringent plate 3, FIG. 3, is linearly (or circularly) polarized with the plane of vibration inclined by 45° to the face of plate 3 and to the optic axis of the measurement system. Consequently, two wavefronts of the sample amplitude are generated, which travel through the plate with different velocities, depending on the state of birefringence. The resulting state of polarization of primary beam changes from the linear to the elliptical, again to the linear state, and so on. Consequently, several nodal points are produced along the path of primary beam where the state of polarization is given by a vector inclined by the angle of 45° to the face of plate. According to Rayleigh model of light scattering, FIG. 2, the intensities of scattered light are simply related to the azimuthal angles when the observation angles are equal to 90°, and are maximum or minimum when the azimuthal angles are equal to 90°, or 0°, respectively. Such minima and maxima of intensity of scattered radiation exist at the points where the amount of birefringence R, expressed in terms of the wavelength $\lambda$ is equal to $R=m\lambda$ where $m=0, 1, 2, 3, \ldots$, or $\frac{1}{2}, 1+\frac{1}{2}, \ldots$, respectively. Performing the observation under two azimuthal angles, in direction normal to the incident light beam, and observing the light intensity distribution in two selected scattered light sheets, as shown in FIG. 3, one obtains two complementary sets of light intensity maxima and minima along the path of primary light beam which are related to the same values of the observation and azimuthal angles of each point along the line of measurements, that is which are related to two particular sheets of the scattered light. This technique of observation increases the resolution and accuracy of measurements.

To assure that the above stated condition regarding the values of observation and azimuthal angles are satisfied, a particular means, called scattered light primary selector is invented and a particular lens is located in a scattered light path. The scattered light primary selector, FIGS. 4 and 5, selects three sheets of light scattered under the azimuthal angles equal to 0°, 90° and 45° with respect to the vibration plane of the impinging primary beam, or under the azimuthal angles equal to −45°, +45° and 0° with respect to the normal to the face of plate. The central light sheet, 22, of constant light intensity carries information on the location of the primary beam 21; two outer light sheets, 23 and 24, of varying light intensity, carry complementary information on the amount of birefringence accumulated along the path of primary beam light. The secondary scattered light selector 6 (or selecting lens) assures that only the rays scattered under the observation angle close to 90° are allowed to reach the recording or displaying means, FIG. 6.

Details of the Invention

Referring to FIG. 1 of the drawings, the light source, e.g. a laser, produces a very narrow light beam; the means 2 polarizes the light beam in a plane of a selected orientation; this light enters the birefringent body 3, which scatters the primary beam light in all directions; the means 4 performs a primary selection of three sheets of scattered light described in the point 5.1; the means 5 transmits either selected one, or two, or all three sheets of light selected by the means 4; the means 6 together with the means 7 performs the secondary selection of the light rays contained in selected light sheets; the means 8 displays or/and records the selected signal (light intensity) carried by the selected light sheet(s).

Figure 2:
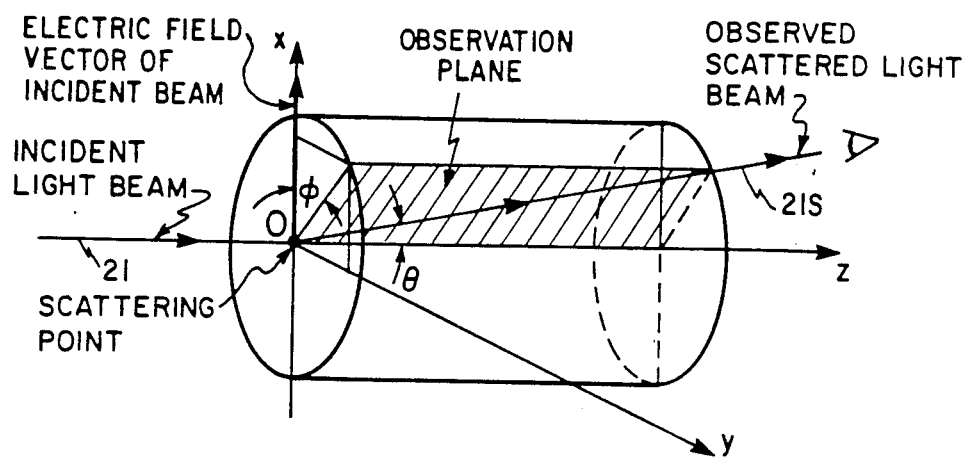
FIG. 2 is optical foundation of measurement principle (Rayleigh model of scattering), and illustrates the influence of major parameters, the observation angle $\theta$ and the azimuthal angle $\phi$.
Figure 3:
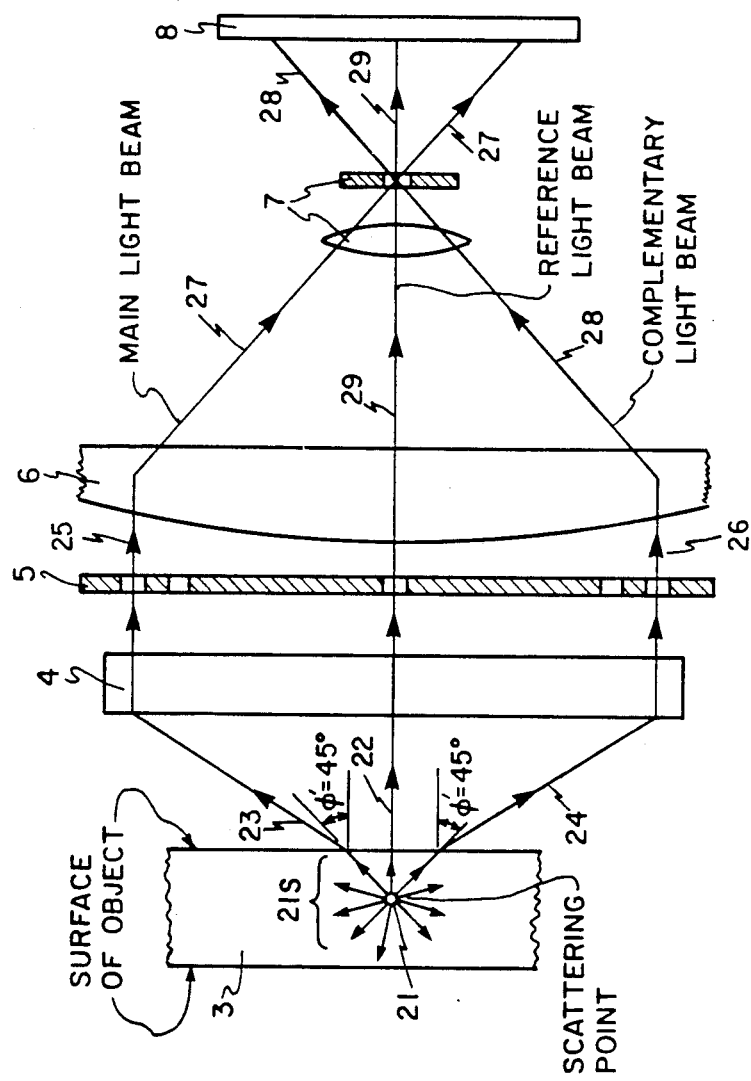
FIG. 3 is principle of measurements using three related light sheets scattered from the same light beam along its path in the body when the electric field vector of the polarized primary light beam makes the angle of 45 with the direction of the optic axis of the system.

Referring to FIG. 2 of the drawings, the sketch presents a typical scheme of Rayleigh model of light scattering; the pertinent formulas given in textbooks on optics explain the necessity of chosing the observation angles close to 90°, and the azimuthal angles close to 0° or 90°.

FIG. 3 illustrates the physical process presented schematically in FIG. 1. The position of the primary light beam 21, can be chosen arbitrarily with respect to the body 3.

Figure 4:
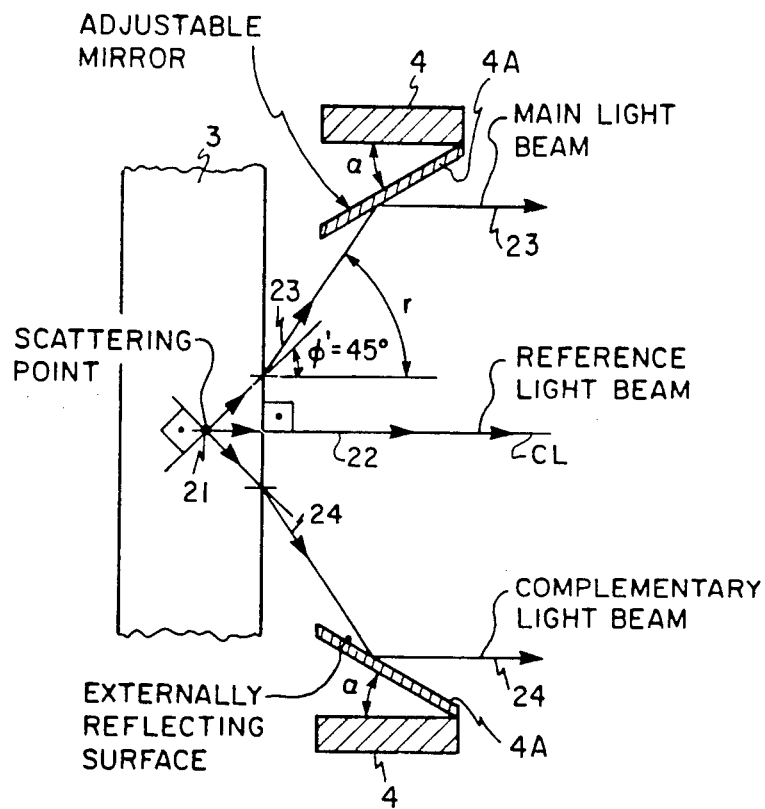
FIG. 4 is principal features of the internal selector.
Figure 5:
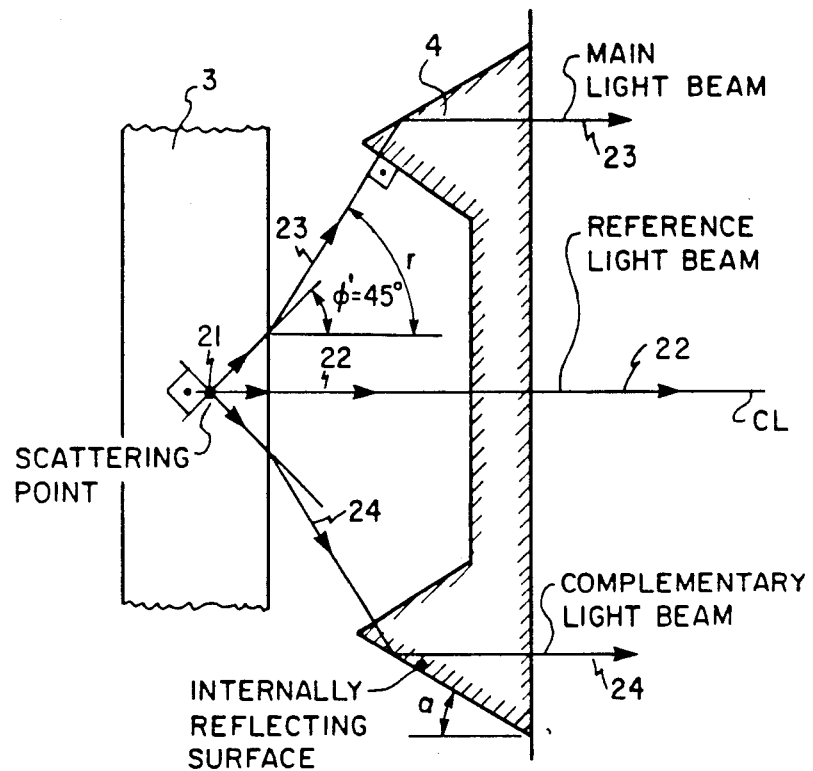
FIG. 5 is principal features of external selector.

The major functional features of the scattered light primary selector are given in FIG. 4 and FIG. 5. This selector selects three sheets of scattered light and collimates them: the emerging light sheets, containing the parallel and not parallel light rays, are parallel. Two basic solutions are invented: the internally reflecting primary selector with adjustable mirrors, FIG. 4, and the externally reflecting primary selector, FIG. 5. The reflecting surfaces are either made of dielectics or of metals or metallized dielectric surfaces. The indices of refraction of the dielectric reflecting surfaces are chosen according to the transfer function of the optical system, to optimize the signal/noise ratio. The metallic or metallized reflecting surfaces are made as reflective phase retarders to also optimize the signal/noise ratio.

Figure 6:
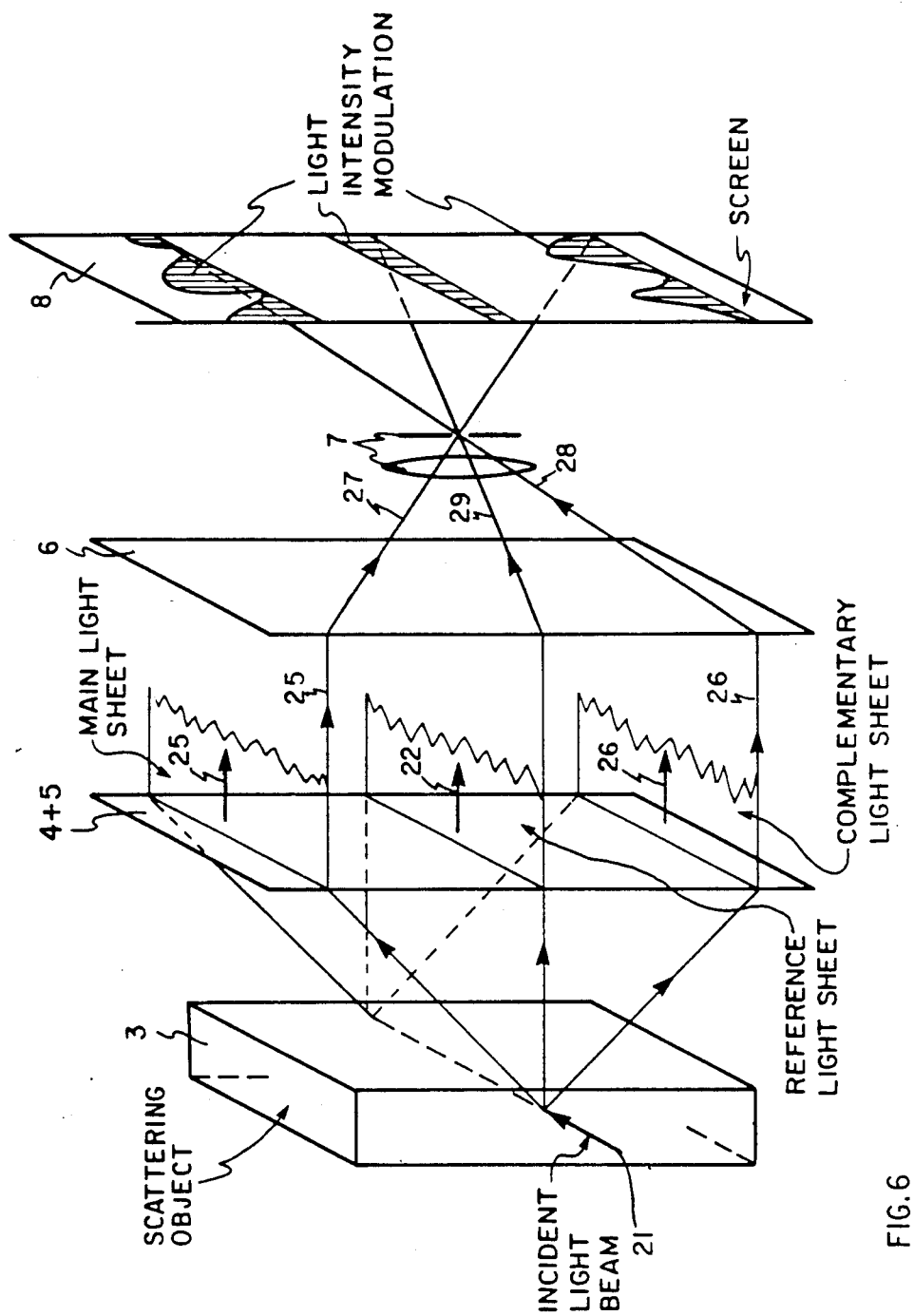
FIG. 6 is an example of an intensity modulation of the output signals presented by three selected light sheets which carry information on the location of primary light beam, and supply two complementary pieces of information on the state of birefringence along the path of primary beam.

FIG. 6 illustrates formation of the image of the scattered light intensity distributions along the path of primary beam (line of measurement) in chosen azimuthal angles, for observation angle close to 90° at each scattering point. Such intensity distributions carry directly information on the state of birefringence in a birefringent body, along chosen lines. From the point of view of the experimental stress analysis of plane stress fields, these lines represent cross-sections through the isodyne field; such cross-sections yield directly the values of the normal and shear stress components along the lines of measurements.

I claim:

1. Apparatus for measuring state of optical anisotropy or birefringence in solid and liquid bodies comprising (1) a source of radiant energy producing a single, narrow, collimated, primary light beam, circularly or linearly polarized with an adjustable plane of vibration, which is directed into the said body along any selected line of measurement; (2) means for collecting and collimating three primary light sheets-a main light sheet, a complementary light sheet, and a reference light sheet-consisting of light scattered in the said body from the said primary light beam along the line of measurement, the angles between the direction of polarization of the primary light beam given by the direction of the electric field vector and the said three primary light sheets being equal to or close to 0°, 45° and 90°, respectively, where the said primary light sheets consist of scattered light beams carrying information on the state of optical anisotropy or birefringence at each scattering point along the line of measurement; (3) selecting and focusing means for elimination from the said three primary light sheets of all light beams which are scattered under angles oblique to the line of measurement so the resulting three secondary light sheets only consist of originally parallel light beams scattered in the direction normal to the primary light beam which are focused by the said means; (3) means for displaying or recording the distributions of the intensities of light scattered along the line of measurement in the directions given by the said three azimuthal angles using the said three sheets of scattered light.

2. The apparatus of claim 1 in which the radiant energy is light from a laser, in the visible or infrared bands.

3. The apparatus of claim 1 in which the radiant energy is in microwave band.

4. The apparatus of claim 1 in which the means for collecting and collimating three primary light sheets allows collection, selection and collimation of three primary light sheets consisting of light beams scattered in the said body along the path of the said beam at arbitrarily selected azimuthal angles wherein all the said three scattered light sheets carry information on the state of birefringence along the line of measurement, and the middle of the said three sheets fixes the position of the line of measurement.

5. The apparatus of claim 1 in which the said selecting and focusing means comprises: (1) a field lens of diameter larger than the measurement region of the said optically anisotropic body, where the lens axis is normal to the object plane and image plane, which assures that the said secondary light sheets only consist of rays scattered in a direction normal to the line of measurement at each scattering point, that is, at observation angles equal to 90°; (2) a linear polarizing filter to eliminate undesirable information contained in the said primary light sheets; (3) an adjustable aperture situated on the axis of the said field lens; (4) an image-forming lens or optics.

6. The apparatus of claim 1 in which the means for collecting and collimating of the said three primary light sheets comprises: (1) two adjustable externally reflecting surfaces, either dielectric or conducting, to collimate the said two outer primary light sheets; (2) a noise-reducing screen, called a screen filter, with three slits which allow transmission of the said three light sheets or of any one of them.

7. The apparatus of claim 1 in which the means for collecting and collimating the said primary light sheets comprises: (1) a dielectric prism with two internally reflecting surfaces, either coated or uncoated, to collimate the said two outer sheets wherein the said outer sheets and the middle sheet as well enter the prism at right angles through the surfaces of the said prism; (2) a noise-reducing screen with three slits which allow transmission of the said three sheets.

8. The apparatus of claim 6 or 7 in which the reflecting surfaces of the means for collecting and collimating are suitably coated to produce the reflective phase retarders for selected wavelengths to separate the information of interest or to optimize the signal/noise ratio.

* * * * *